United States Patent [19]

Prat et al.

[11] Patent Number: 5,718,891
[45] Date of Patent: Feb. 17, 1998

[54] PROCESS FOR THE PRODUCTION OF SOLID ESTERQUATS WITH IMPROVED DISPERSIBILITY IN WATER

[75] Inventors: Esther Prat, Alella; Joaquim Bigorra, Sabadell, both of Spain

[73] Assignee: Henkel Kommanditgesellschaft auf Aktien, Duesseldorf, Germany

[21] Appl. No.: 318,864

[22] PCT Filed: Nov. 10, 1993

[86] PCT No.: PCT/EP93/03152

§ 371 Date: Dec. 19, 1994

§ 102(e) Date: Dec. 19, 1994

[87] PCT Pub. No.: WO94/21593

PCT Pub. Date: Sep. 29, 1994

[30] Foreign Application Priority Data

Mar. 18, 1993 [DE] Germany .......... 43 08 794.9

[51] Int. Cl.$^6$ .................. A61K 7/06; A61K 7/00
[52] U.S. Cl. .............. 424/70.28; 424/70.1; 514/506; 514/642
[58] Field of Search ............... 424/70.28, 70.1; 514/506, 642

[56] References Cited

U.S. PATENT DOCUMENTS 5,494,659  2/1996  Salka et al. ............ 924/70.13

FOREIGN PATENT DOCUMENTS

| | | |
|---|---|---|
| 0008839 | 3/1980 | European Pat. Off. . |
| 3527974 | 2/1987 | Germany . |
| 4039950 | 6/1992 | Germany . |
| 4103489 | 8/1992 | Germany . |
| 4138630 | 5/1993 | Germany . |
| 9101295 | 2/1991 | WIPO . |

OTHER PUBLICATIONS

Parf. Kosm. 56, 157 (1975).
C.R. CED Congress, Barcelona, 167 (1992).
C.R. CED Congress, Sitges, 59 (1993).
Bull. soc. Chim. France, 333 (1949).

*Primary Examiner*—Sally Gardner-Lane
*Attorney, Agent, or Firm*—Wayne C. Jaeschke; John E. Drach; Henry E. Millson, Jr.

[57] ABSTRACT

Solid esterquats with improved dispersibility in water are obtained by quaternizing fatty acid triethanolamine esters with alkylating agents in known manner in the presence of a) dispersants selected from the group consisting of fatty alcohols, fatty acid monoglycerides and dialkyl ethers and optionally b) emulsifiers selected from the group consisting of fatty alcohol polyglycol ethers, fatty acid monoglyceride polyglycol ethers, fatty acid oligoglyceride polyglycol ethers, polysorbates and alkyl oligoglucosides.

The products are suitable, for example, for the production of hair-care preparations.

13 Claims, No Drawings

PROCESS FOR THE PRODUCTION OF SOLID ESTERQUATS WITH IMPROVED DISPERSIBILITY IN WATER

BACKGROUND OF THE INVENTION

This application claims priority to PCT/EP93/03152 Nov. 10, 1993 under 35 USC 371 and a priority to Mar. 18, 1993 under 35 USC 119.

1. Field of the Invention

This invention relates to solid esterquats with improved dispersibility in water which are obtained by quaternizing fatty acid triethanolamine esters in the presence of dispersants and optionally emulsifiers, to hair-care preparations containing these compounds and to the use of the compounds for the production of hair-care preparations.

2. Statement of Related Art

Damage to the structure of hair is caused by frequent bleaching, permanent waving, dyeing, over exposure to UV light, washing with degreasing surfactants and normal ageing. The hair becomes brittle and loses its shine. In addition, the hair develops an electrostatic charge on combing while the roughened surface of the hair gives rise to matting and knotting so that the hair becomes difficult to comb. Accordingly, hair-care preparations with a combability-improving effect have acquired considerable significance in the cosmetics field. Preparations such as these may be applied to the hair still wet from washing in the form of a rinse, an aerosol foam or even in the form of emulsions (cream rinses) and may either be rinsed out after a contact time of a few minutes or may be left on the hair.

Cationic surfactants, more particularly quaternary ammonium compounds, such as for example distearyl dimethylammonium chloride (DSDMAC), either on their own or in combination with various wax-like additives, such as hydrocarbons, fatty alcohols or fatty acid esters, have been successfully used as active substances for improving hair structure [Parf. Kosm. 56, 157 (1975)]. Unfortunately, the cationic surfactants mentioned have the disadvantage of inadequate biodegradability so that, on introduction into surface waters, they can gradually impair the viability of aquatic biocenoses.

In addition, German patent application DE-A1 35 27 974 describes esters of betaine with fatty alcohols or fatty alcohol polyglycol ethers for use in acidic hair-care preparations. Although the betaine esters show high ecotoxicological compatibility, they are unsatisfactory in regard to improving combability, antistatic behavior, feel and rinsing behavior and, in addition, are not stable to hydrolysis at acidic pH values.

In their earlier German patent application DE-A1 41 38 630, applicants proposed using quaternized fatty acid triethanolamine ester salts, so-called "esterquats", as cationic surfactants in acidic hair-care preparations. However, it was found in practice that both the dispersibility of these products in water and their stability in storage are not always entirely satisfactory.

Accordingly, the problem addressed by the present invention was to provide a process for the production of esterquats with improved dispersibility in water and higher stability in storage which could be used with advantage in hair-care preparations.

DESCRIPTION OF THE INVENTION

The present invention relates to a process for the production of solid esterquats with improved dispersibility in water, in which fatty acid triethanolamine esters are quaternized with alkylating agents in known manner in the presence of a) dispersants selected from the group consisting of fatty alcohols, fatty acid monoglycerides and dialkyl ethers and optionally b) emulsifiers selected from the group consisting of fatty alcohol polyglycol ethers, fatty acid monoglyceride polyglycol ethers, fatty acid oligoglyceride polyglycol ethers, polysorbates and alkyl oligoglucosides.

It has surprisingly been found that the quaternization of fatty acid triethanolamine esters can also be carried out in the presence of the dispersants and, optionally, emulsifiers mentioned above. Solvent-free and, in particular, alcohol-free, solid esterquats readily dispersible in water are obtained in this way. The invention includes the observation that the subsequent addition of the dispersants mentioned to conventionally produced esterquats improves dispersibility in water only very slightly, if at all. Another advantage is that aqueous solutions of the esterquats obtainable by the process according to the invention are particularly stable in storage, i.e. remain homogeneous and show constant viscosity, even in the event of prolonged storage. After dissolution in water, products to which dispersants and emulsifiers have actually been added during the quaternization process directly give a hair-care preparation which exhibits excellent performance properties.

Esterquats and fatty acid triethanolamine esters

Esterquats are a known group of cationic surfactants which are typically obtained by esterification of triethanolamine or triethanolamine polyglycol ethers with fatty acids and subsequent quaternization in organic solvents. The production and properties of esterquats are described, for example, in WO 91/01295 (Henkel) and in the synoptic articles by O. Ponsati in C.R. CED Congress, Barcelona, 167 (1992) and R. Puchta in C.R. CED Congress, Sitges, 59 (1993).

Fatty acid triethanolamine esters corresponding to formula (I):

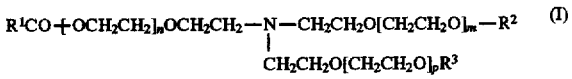

in which $R^1CO$ is a saturated and/or unsaturated acyl radical containing 6 to 22 carbon atoms, $R^2$ and $R^3$ independently of one another represent hydrogen or $R^1CO$ and n, m and p together have a value of 0 or 1 to 10, are used as starting materials in the process according to the invention for the production of the esterquats.

Technical monoester/diester/triester mixtures in which the degree of esterification is between 1.2 and 2.2 and preferably between 1.5 and 1.9 are preferably used. Esters which are derived from technical $C_{12/18}$ or $C_{16/18}$ fatty acids, such as, for example, palm oil fatty acid, coconut oil fatty acid or tallow fatty acid, and which may have an iodine value of 0 to 40 are preferably used.

Dispersants

Suitable dispersants are, in particular, fatty alcohols corresponding to formula (II):

in which $R^3$ is an alkyl and/or alkenyl radical containing 12 to 22 carbon atoms.

Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained, for example, in the high-pressure hydrogenation of fatty acid methyl esters or aldehydes from Roelen's oxo synthesis. Technical coconut oil or tallow fatty alcohols containing 12 to 18 and preferably 16 to 18 carbon atoms are preferably used.

Other suitable dispersants are fatty acid monoglycerides corresponding to formula (III):

in which $R^4CO$ represents saturated and/or unsaturated acyl radicals containing 12 to 22 carbon atoms.

Typical examples are monoglycerides of lauric acid, myristic acid, palmitic acid, palmitoleic acid, stearic acid, isostearic acid, oleic acid, elaidic acid, petroselic acid, arachic acid, gadoleic acid, behenic acid and erucic acid and the technical mixtures thereof obtained, for example, in the pressure hydrolysis of fats and oils. Monoglycerides of lauric acid, palmitic acid, stearic acid and/or oleic acid are preferably used. The monoglycerides are also known compounds which are obtained, for example, by transesterification of beef tallow or new sunflower oil and subsequent concentration by molecular distillation. Technical monoglycerides which may have a total diglyceride and triglyceride content of less than 40% by weight are normally used.

Finally, other suitable dispersants are dialkyl ethers corresponding to formula (IV):

in which $R^5$ and $R^6$ independently of one another represent alkyl and/or alkenyl radicals containing 6 to 22 carbon atoms.

These dialkyl ethers are also known compounds which may be obtained by the relevant methods of preparative organic chemistry. Processes for their production, for example by condensation of fatty alcohols in the presence of p-toluenesulfonic acid, are known for example from *Bull. Soc. Chim. France*, 333 (1949), DE-A1 40 39 950 (Hoechst) and DE-A1 41 03 489 (Henkel). Symmetrical dialkyl ethers containing 6 to 12 carbon atoms in the alkyl radicals are preferred from the applicational point of view. Dialkyl ethers corresponding to formula (IV), in which $R^5$ and $R^6$ represent octyl and/or 2-ethylhexyl radicals, have proved to be particularly advantageous. Accordingly, the dialkyl ethers particularly preferred for the purposes of the invention are di-n-octyl ether and di-2-ethylhexyl ether.

Emulsifiers

Suitable emulsifiers are, for example, fatty alcohol polyglycol ethers corresponding to formula (V):

in which $R^7$ is an alkyl radical containing 12 to 22 carbon atoms and q is a number of 10 to 40.

Typical examples are adducts of on average 10 to 40 moles and preferably 20 to 25 moles of ethylene oxide with fatty alcohols containing 12 to 22 and preferably 16 to 18 carbon atoms such as, for example, cetostearyl alcohol 20 EO adduct or isostearyl alcohol 25 EO adduct, which may have a conventional or narrow homolog distribution.

Other suitable emulsifiers are adducts of on average 10 to 40 moles of ethylene oxide with fatty acid monoglycerides corresponding to formula (VI):

in which $R^8CO$ is an acyl radical containing 12 to 18 carbon atoms. Typical examples are adducts of on average 10 to 40 moles and preferably 20 to 25 moles of ethylene oxide with technical lauric acid monoglyceride, palmitic acid monoglyceride, stearic acid monoglyceride and/or oleic acid monoglyceride.

Other suitable emulsifiers are fatty acid oligoglyceride polyglycol ethers, i.e. adducts of on average 10 to 40 moles and preferably 20 to 25 moles of ethylene oxide with esters of fatty acids containing 12 to 18 carbon atoms with technical oligoglycerol mixtures. Typical examples are adducts of ethylene oxide with mono-, di-, tri-, tetra- and/or pentaesters of di-, tri-, tetra-, penta- and/or oligoglycerol with lauric acid, palmitic acid, stearic acid and/or oleic acid.

Other suitable emulsifiers are polysorbates, i.e. adducts of on average 10 to 40 moles of ethylene oxide with sorbitan esters of which the fatty acid component is derived from lauric acid, palmitic acid, stearic acid and/or oleic acid. Typical examples are adducts of on average 10 to 40 moles and preferably 20 to 25 moles of ethylene oxide with mono-, di-, sesqui- and/or triesters of sorbitan with lauric acid, palmitic acid, stearic acid and/or oleic acid.

Finally, other suitable emulsifiers are alkyl oligoglucosides corresponding to formula (VII):

in which $R^9$ is an alkyl radical containing 6 to 22 carbon atoms, G is a sugar unit containing 5 or 6 carbon atoms and z has a value of 1 to 10.

Typical examples are alkyl oligoglucosides corresponding to formula (VII) in which $R^9$ is an alkyl radical containing 8 to 18 and preferably 12 to 14 carbon atoms and z has a value of 1.1 to 1.7.

As explained above, the primary objective of the invention is to produce a readily dispersible esterquat to which the dispersant and optionally the emulsifier are added during the actual production process. Apart from the applicational advantages already mentioned, the otherwise necessary use of an organic solvent in the quaternization stage is elegantly avoided in this way.

The esterquats according to the invention may normally contain the dispersants in such quantities that they make up from 10 to 90% by weight and preferably from 50 to 70% by weight of the end product. The emulsifiers may make up from 0 to 30% by weight and preferably from 5 to 20% by weight of the end product. In practice, this means that the alkylation reaction is carried out in the presence of at least one dispersant. However, the invention also includes the possibility that the alkylation reaction may also be carried out in the presence of at least one dispersant and one emulsifier. To establish a desired content of dispersant or emulsifier in the end product, the calculated quantity of dispersant or emulsifier must be added to the ester before the quaternization reaction. Calculation of the necessary ratios can be left to the expert without any need for inventive activity.

Alkylation

The alkylation of the fatty acid triethanolamine esters may be carried out in known manner. To this end, the ester is initially introduced into the reactor and stirred with the alkylating agent (which is typically used in equimolar quantities or in a slight excess) at elevated temperatures. On completion of the reaction, unreacted alkylating agent may be destroyed by addition of a small quantity of amino acid, preferably glycine. Suitable alkylating agents in this regard are alkyl halides, dialkyl sulfates and ethylene oxide—the latter in the presence of dialkyl phosphates. The process according to the invention is preferably applicable to methyl-quaternized esterquats in the form of their chlorides or methyl sulfate salts and to esterquat salts which have been quaternized with 1 to 5 moles of ethylene oxide.

Hair care preparations

The present invention also relates to hair-care preparations containing 14 to 86% by weight of quaternized fatty acid triethanolamine ester salts, 14 to 86% by weight of dispersants and 5 to 30% by weight of emulsifiers, with the proviso that the percentages add up to 100% by weight.

In the process according to the invention, the hair-care preparations are directly obtained by quaternizing the fatty acid triethanolamine esters in the presence of the corresponding quantities of dispersants and emulsifiers and subsequently dissolving or dispersing the reaction product in water. However, the solid esterquats, which only contain the dispersant component, may also be dissolved in water and the emulsifier subsequently incorporated by mixing.

Hair-care preparations in the context of the invention are, for example, shampoos, rinses, setting lotions and the like. The hair-care preparations preferably have a pH value of 3 to 5, preferably from 3 to 4.

Industrial Applications

The products obtainable by the process according to the invention are readily dispersible in water. The dispersions or emulsions are homogeneous and stable in storage and exhibit excellent applicational properties in regard to improving the combability and reducing the electrostatic charging of hair.

Accordingly, the present invention also relates to the use of the solid esterquats obtainable by the process according to the invention for the production of hair-care preparations in which they may be present in quantities of 70 to 100% by weight and preferably 80 to 90% by weight, based on the solids content of the preparation.

The following Examples are intended to illustrated the invention without limiting it in any way.

EXAMPLES

I. Production Examples a) Esterification.

324 g (1.2 moles) of partly hydrogenated $C_{16/18}$ tallow fatty acid (iodine value 40), 149 g (1 mole) of triethanolamine and 1.4 g of 50% by weight hypophosphorous acid were introduced into a 1-liter three-necked flask equipped with a stirrer, internal thermometer and distillation head. The reaction mixture was heated over a period of 4 h to a temperature of 160° C. under a reduced pressure of 40mbar until the acid value was below 5. The red tallow fatty acid triethanolamine ester was then cooled, the reaction mixture was vented and i liter of air was passed through for 15 minutes with continuous stirring.

b) Quaternization

A mixture of 45 g (0.1 mole) of the ester from a) in 105 g of dispersant A ($C_{16/18}$ tallow fatty alcohol) B (glycerol monostearate) or C (di-n-octyl ether) was introduced into and heated with stirring to 45° C. in a 500 ml three-necked flask equipped with a stirrer, dropping funnel and reflux condenser (ratio by weight of esterquat to dispersant 30:70). 12 g (0.095 mole) of dimethylsulfate were added dropwise over a period of 2 h. After the addition, the mixture was stirred for another 2 h at 60° C. and unreacted DMS was destroyed by addition of 0.4 g (0.005 mole) of glycine. The water-free esterquat/dispersant mixture was obtained in the form of a light-colored, wax-like mass which was then mechanically converted into flakes.

II. Application Examples

The water-free solid esterquats from I) were incorporated in an acidic hair rinse having the following formulation:

Esterquat: 5.7% by weight

Emulsifier: 0.5% by weight

Water: ad 100% by weight

Cetostearyl alcohol 20 EO (Eumulgin® B2, a product of Henkel KGaA, Düsseldorf, FRG) was used as emulsifier; the pH value of the rinses was adjusted to 3.5. Emulsification took place with gentle stirring at room temperature. Homogeneous, cosmetically elegant emulsions were obtained in every case. The viscosity of the emulsions was determined after storage for 1, 2 and 15 d (Brookfield RVT, 20° C., 10 r.p.m.). The results are set out in Table 1:

TABLE 1

Viscosity measurements

| Ex. | Esterquat | Dispersant | Viscosity (mPas) | | |
|---|---|---|---|---|---|
| | | | 1 d | 2 d | 15 d |
| 1 | A1 | A | 9000 | 9400 | 8250 |
| 2 | A2 | B | 9100 | 9300 | 8300 |
| 3 | A3 | C | 9050 | 9350 | 8300 |

For comparison, a commercial esterquat (Dehyquart® AU 36, 90% by weight in isopropyl alcohol, a product of Pulcra S. A., Barcelona/Spain) was first freed from the solvent, subsequently mixed with dispersant A, B or C and used in the starting formulation mentioned.

In all three tests, it was found that, comparatively, much more intensive shearing was required for emulsification. Although the comparison emulsions initially showed similar viscosity values, they underwent a rapid reduction in viscosity after brief storage.

What is claimed is:

1. A process for the production of solid esterquats with improved dispersibility in water comprising reacting a fatty acid triethanolamine ester of the formula:

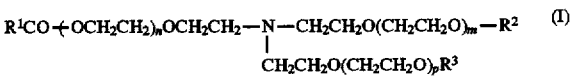

wherein $R^1CO$ is a saturated and/or unsaturated acyl radical having from about 6 to about 22 carbon atoms; each of $R^2$ and $R^3$ is independently hydrogen or $R^1CO$; and n, m and p together have a value of 0 to 10 with an alkylating agent in the presence of a dispersant selected from the group consisting of a fatty alcohol of the formula (III):

wherein $R^3$ is an alkyl and/or alkenyl group having from about 12 to about 22 carbon atoms and a dialkyl ether of the formula (IV)

$$R^5\text{—}O\text{—}R^6$$

wherein $R^5$ and $R^6$ is independently an alkyl and/or alkenyl group having from about 6 to about 22 carbon atoms; and from 0% to about 30% by weight, based on the esterquat, of an emulsifier selected from the group consisting of a fatty alcohol polyglycol ether, a fatty acid monoglyceride polyglycol ether, a fatty acid oligoglyceride polyglycol ether, a polysorbate, and an alkyl oligoglucoside.

2. The process of claim 1 wherein said emulsifier is a fatty alcohol polyglycol ether of the formula (V):

$$R^7O\text{—}(CH_2CH_2O)_qH \qquad (V)$$

wherein $R^7$ is an alkyl group having from about 12 to about 22 carbon atoms and q is a number from 10 to 40.

3. The process of claim 1 wherein said emulsifier is a fatty acid monoglyceride of the formula (VI):

$$\begin{array}{c}\text{OH}\\|\\\text{OH—CH}_2\text{—CH—CH}_2\text{—OCOR}^8\end{array} \qquad (VI)$$

ethoxylated with from about 10 moles to about 40 moles of ethylene oxide and wherein $R^8CO$ is an acyl radical having from about 12 to about 18 carbon atoms.

4. The process of claim 1 wherein said dispersant is the adduct of an ester of a fatty acid having from about 12 to about 18 carbon atoms ethoxylated with from about 10 to 40 moles of ethylene oxide and a technical oligoglycerol mixture.

5. The process of claim 1 wherein the amount of said dispersant is from about 10% to about 90% by weight, based on the esterquat.

6. The process of claim 1 wherein said alkylating agent is an alkyl halide, a dialkylsulfate, or ethylene oxide.

7. A hair care composition comprising from about 14% to about 86% by weight of quaternized fatty acid triethanolamine ester salts made by the process of claim 1; from about 14% to about 86% by weight of a dispersant selected from the group consisting of a fatty alcohol of the formula (III):

$$R^3\text{—}OH \qquad (III)$$

wherein $R^3$ is an alkyl and/or alkenyl group having from about 12 to about 22 carbon atoms and a dialkyl ether of the formula (IV)

$$R^5\text{—}O\text{—}R^6$$

wherein $R^5$ and $R^6$ is independently an alkyl and/or alkenyl group having from about 6 to about 22 carbon atoms and from about 5% to about 30% by weight of an emulsifier selected from the group consisting of a fatty alcohol polyglycol ether, a fatty acid monoglyceride polyglycol ether, a fatty acid oligoglyceride polyglycol ether, a polysorbate and an alkyl oligoglucoside; wherein the quaternized fatty acid triethanolamine ester salts were quaternized in the presence of the dispersant and the emulsifier.

8. The process of claim 1 wherein from about 5 to about 30% by weight of emulsifier is present.

9. The process of claim 8 wherein said emulsifier is an alkyl oligoglucoside of the formula (VII):

$$R^9O\text{—}(G)_z \qquad (VII)$$

wherein $R^9$ is an alkyl group having from about 6 to about 22 carbon atoms, G is a sugar unit having from 5 or 6 carbon atoms and z has a value of 1 to 10.

10. The process of claim 8 wherein from about 5 to about 20% by weight of emulsifier is present.

11. The process of claim 5 wherein from about 50 to about 70% by weight of dispersant is present.

12. The composition of claim 7 wherein the emulsifier is an alkyl oligoglucoside of the formula (VII):

$$R^9O\text{—}(G)_z \qquad (VII)$$

wherein $R^9$ is an alkyl group having from about 6 to about 22 carbon atoms, G is a sugar unit having from 5 or 6 carbon atoms and z has a value of 1 to 10.

13. The process of claim 5 wherein from about 5 to about 30% by weight of emulsifier is present.

* * * * *